(12) United States Patent
Satoh et al.

(10) Patent No.: US 9,108,871 B2
(45) Date of Patent: Aug. 18, 2015

(54) SELECTIVE HYDROGEN ADDING EQUIPMENT FOR LIVING ORGANISM APPLICABLE FLUID

(75) Inventors: Fumitake Satoh, Kanagawa (JP); Tomoki Seo, Kanagawa (JP); Ryosuke Kurokawa, Kanagawa (JP); Bunpei Satoh, Kanagawa (JP); Tatsuya Naito, Kanagawa (JP); Tomoyuki Yanagihara, Kanagawa (JP); Yohei Satoh, Kanagawa (JP); Yoko Satoh, Kanagawa (JP)

(73) Assignee: MIZ Co. LTD., Fujisawa, Kanagawa (JP)

( * ) Notice: Subject to any disclaimer, the term of this patent is extended or adjusted under 35 U.S.C. 154(b) by 383 days.

(21) Appl. No.: 13/491,435

(22) Filed: Jun. 7, 2012
(Under 37 CFR 1.47)

(65) Prior Publication Data

US 2013/0112600 A1   May 9, 2013

Related U.S. Application Data

(63) Continuation of application No. PCT/JP2011/065879, filed on Jul. 12, 2011.

(30) Foreign Application Priority Data

Jul. 14, 2010   (JP) ................ 2010-159979

(51) Int. Cl.
*B01D 19/00*   (2006.01)
*B65B 29/06*   (2006.01)
(Continued)

(52) U.S. Cl.
CPC . *C02F 1/685* (2013.01); *A23L 2/54* (2013.01); *B01D 19/0063* (2013.01);
(Continued)

(58) Field of Classification Search
CPC .............. C02F 1/68; C02F 1/683; C02F 1/70; C02F 1/705; C02F 1/685; C02F 2305/06; C02F 1/688; B01D 19/00; B01D 19/0063; B65B 29/06; B65D 85/72; C01B 5/00
USPC ........... 96/155; 210/97, 188, 198.1, 205, 206; 422/1, 20, 211; 423/580.1; 252/1, 175; 424/682; 426/66, 74
See application file for complete search history.

(56) References Cited

U.S. PATENT DOCUMENTS 6,251,259 B1 * 6/2001 Satoh et al. .................. 205/744
7,252,771 B2   8/2007 Kopinke et al.
(Continued)

FOREIGN PATENT DOCUMENTS

CN   101142143 A   3/2008
EP   1421988   5/2004
(Continued)

*Primary Examiner* — Joseph Drodge
(74) *Attorney, Agent, or Firm* — Muncy, Geissler, Olds & Lowe, P.C.

(57) ABSTRACT

A selective hydrogen adding equipment for living organism applicable fluid, comprising a hydrogen generating system and a hydrogen bubble forming implement, the hydrogen bubble forming implement having a gas/liquid separating section including an open-close type valve, wherein the hydrogen bubble forming implement is disposed in a closed container storing living organism applicable fluid and the hydrogen gas is supplied into the closed container storing living organism applicable fluid via the gas/liquid separating section thereby to provide living organism applicable hydrogen-contained fluid, and wherein the open-close type valve is opened by a gas pressure of hydrogen gas generated in an internal of the hydrogen bubble forming implement owing to a reaction between the hydrogen generating system and the generating-purpose water thereby to exhaust hydrogen gas into the closed container as an external of the hydrogen bubble forming implement while the open-close type valve is closed after the exhaust.

1 Claim, 4 Drawing Sheets

(51) Int. Cl.
  *B65D 85/72* (2006.01)
  *C02F 1/68* (2006.01)
  *C02F 1/70* (2006.01)
  *A23L 2/54* (2006.01)
  *C01B 3/06* (2006.01)
  *C01B 3/08* (2006.01)

(52) U.S. Cl.
  CPC .............. *C01B 3/065* (2013.01); *C01B 3/08* (2013.01); *C02F 1/68* (2013.01); *C02F 1/688* (2013.01); *C02F 1/705* (2013.01); *C02F 1/70* (2013.01); *C02F 2305/06* (2013.01); *Y02E 60/362* (2013.01)

(56) References Cited

U.S. PATENT DOCUMENTS

| | | | | |
|---|---|---|---|---|
| 8,038,127 | B2* | 10/2011 | Matsuoka et al. | 261/21 |
| 8,460,861 | B2* | 6/2013 | Satoh et al. | 435/2 |
| 8,663,444 | B2* | 3/2014 | Nabeshima | 204/660 |
| 2003/0132104 | A1* | 7/2003 | Yamashita et al. | 204/252 |
| 2004/0219260 | A1* | 11/2004 | Anderson et al. | 426/2 |
| 2006/0273281 | A1 | 12/2006 | Bagley | |
| 2007/0128104 | A1 | 6/2007 | Hayashi et al. | |
| 2008/0311225 | A1 | 12/2008 | Shiga | |
| 2011/0024361 | A1* | 2/2011 | Schwartzel et al. | 210/739 |
| 2012/0225010 | A1* | 9/2012 | Boyle et al. | 423/657 |

FOREIGN PATENT DOCUMENTS

| | | | |
|---|---|---|---|
| EP | 1867607 | | 12/2007 |
| JP | 3031812 | U | 12/1996 |
| JP | 2002-301483 | | 10/2002 |
| JP | 2002-336877 | | 11/2002 |
| JP | 2004-041949 | | 2/2004 |
| JP | 2004-174301 | * | 6/2004 |
| JP | 2004-243151 | | 9/2004 |
| JP | 2004-344862 | | 12/2004 |
| JP | 2005-7380 | A | 1/2005 |
| JP | 3107624 | U | 2/2005 |
| JP | 2005-118529 | | 5/2005 |
| JP | 2005-161209 | | 6/2005 |
| JP | 2006-255613 | A | 9/2006 |
| JP | 2006-281119 | | 10/2006 |
| JP | 2007-1633 | A | 1/2007 |
| JP | 2007-050399 | | 3/2007 |
| JP | 2007-134600 | | 5/2007 |
| JP | 2007-167696 | A | 7/2007 |
| JP | 2007-301522 | | 11/2007 |
| JP | 3156455 | | 1/2010 |
| JP | 2010-051963 | | 3/2010 |
| JP | 2010-51963 | | 3/2010 |
| JP | 2010-124808 | | 6/2010 |
| JP | 4486157 | | 6/2010 |
| JP | 4486157 | B1 | 6/2010 |
| WO | WO-2010/092770 | A1 | 8/2010 |

\* cited by examiner

SELECTIVE HYDROGEN ADDING EQUIPMENT FOR LIVING ORGANISM APPLICABLE FLUID

BACKGROUND OF THE INVENTION

1. Field of the Invention

The present invention relates to a selective hydrogen adding equipment for living organism applicable fluid.

2. Description of the Related Art

As a method of producing living organism applicable hydrogen-contained fluid, known in the art are a method using a hydrogen water electrolytically generating apparatus for household use and a method causing metal pieces of metal magnesium as a hydrogen generating agent to contact with living organism applicable fluid (Japanese Patent Application Publication No. 2007-167696).

PRIOR ART DOCUMENT(S)

Patent Document(s)

[Patent Document 1] Japanese Patent Application Publication No. 2007-167696

SUMMARY OF THE INVENTION

Problems to be Solved by the Invention

In the case of obtaining living organism applicable hydrogen-contained fluid using hydrogen generating agent, the hydrogen generating agent may possibly change properties of the living organism applicable fluid when dissolving hydrogen molecules into the living organism applicable fluid. For example, if the hydrogen generating agent is metal magnesium, then magnesium ions are dissolved into the living organism applicable fluid to shift the pH thereof toward alkaline side in accordance with the following Formulae (1) and (2) when generating hydrogen.

$$Mg + 2H_2O \rightarrow Mg(OH)_2 + H_2 \quad \text{Formula (1)}$$

$$Mg(OH)_2 \rightarrow Mg^{2+} + 2OH^- \quad \text{Formula (2)}$$

However, it is not desirable in general to change, before and after the hydrogen generating reaction, constituents of the living organism applicable fluid having been already made up naturally or artificially. The change in constituents may in turn lead to alter the flavor of living organism applicable fluid, such as tea and mineral water.

Therefore, an equipment for producing living organism applicable hydrogen-contained fluid is desired which does not change constituents of living organism applicable fluid.

From a viewpoint of the Food Sanitation Act, only "food additives" are officially permitted as additives allowed for contacting with articles of food.

If, however, hydrogen water is attempted to be made using hydrogen generating agent, then the series of both magnesium and hydride as the hydrogen generating agents are to be said as being in noncompliance with the Food Sanitation Act because not permitted as such food additives.

Means for Solving the Problems

Consequently, when making hydrogen water using hydrogen generating agent as an essential constituent, a hydrogen generating system is required to be stored in a container such as plastic container in order that the hydrogen generating system including the hydrogen generating agent is absolutely non-contact with articles of food (living organism applicable fluid).

The hydrogen generating system container is provided therein with an exhaust outlet for exhausting hydrogen gas. This exhaust outlet is attached to the closed container to be located at an upper gas phase section of the container (to avoid the flowing in of water).

The hydrogen gas from the exhaust outlet of the hydrogen generating agent storing container in the closed container is supplied into the closed container gas phase section thereby to replace the gas in the gas phase section with hydrogen gas and enhance the gas phase inner pressure and hydrogen gas concentration.

This pressurized high concentration hydrogen gas is dissolved into the fluid with time to generate high concentration hydrogen water thereby solving the problems.

Moreover, through preparing a hydrogen generating system which contains the hydrogen generating agent such as metal magnesium as an essential constituent, storing the hydrogen generating system in a hydrogen bubble forming implement having a gas/liquid separating section which is devised so as to release hydrogen gas while not making water flow in, and/or to release hydrogen gas while not making water flow out, and causing the hydrogen generating agent and the generating-purpose water to react in the hydrogen bubble forming implement, the hydrogen gas generated from the hydrogen bubble forming implement is supplied to the closed container gas phase section storing the living organism applicable fluid substantially without causing the generating-purpose water having been used for the hydrogen generating reaction to flow out into the living organism applicable fluid, thereby obtaining the living organism applicable hydrogen-contained fluid to solve the problems. Furthermore, high pressure and high concentration hydrogen gas of gas phase is dissolved into the living organism applicable fluid through shaking the closed container, thereby obtaining high concentration or supersaturated living organism applicable hydrogen-contained fluid to solve the problems.

Advantageous Effect of the Invention

By supplying hydrogen into the living organism applicable fluid using such means, living organism applicable hydrogen-contained fluid can be obtained without changing properties of the living organism applicable fluid. Moreover, using such means also allows high concentration hydrogen beverages to be easily produced without altering the flavor of any beverage regardless of locations, such as home, workplace, street, and storefront.

DESCRIPTION OF THE PREFERRED EMBODIMENTS

Figure 1A:
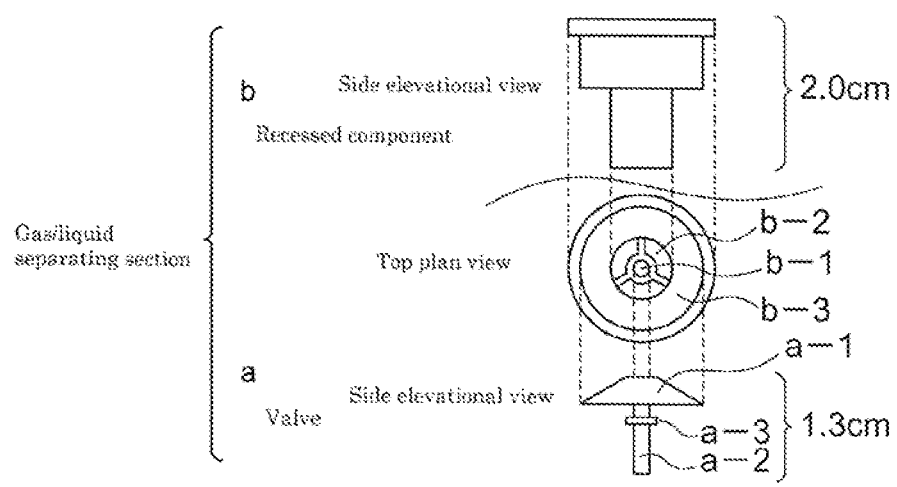
FIG. 1A depicts a plan view and a front elevational view illustrating a gas/liquid separating section according to one embodiment of the present invention.

Hereinafter, embodiments of the present invention will be described.

Living organism applicable fluid in the present invention is a fluid to be applied to living organisms, such as water or water solution, which is an objective to be dissolved therein with hydrogen using the present invention. Examples of living organism applicable fluid include water as well as drinking water and beverages such as tea and coffee. Living organism applicable hydrogen-contained fluid to be obtained by dissolving hydrogen into the living organism applicable fluid is applied to living organisms via inhalation (atomization), drinking, injection, and the like, but is not limited thereto. While an active constituent of the living organism applicable hydrogen-contained fluid and high-concentration or super-saturated living organism applicable hydrogen-contained fluid is hydrogen and the functionality thereof is primarily inhibition of oxidant stress, it is not limited thereto.

Hydrogen generating agent in the present invention is a substance which generates hydrogen. Examples of hydrogen generating agent include substances generating hydrogen by contacting with water, such as metals having higher ionization tendency than hydrogen and hydrogenated compounds including metal hydride. In consideration of excellent reactivity with water, it is preferred to use metal calcium, calcium hydride, metal magnesium, magnesium hydride, or the like. Considering the safety of the resulting reaction products, metal magnesium is particularly preferably used.

Generating-purpose water in the present invention is a liquid for causing hydrogen gas to be generated in a hydrogen bubble forming implement through contacting with the hydrogen generating agent. Examples of such generating-purpose water include tap water, clarified water, ion-exchanged water, purified water, pure water, RO water, and the like, but are not limited thereto. The above-described living organism applicable fluid in itself may also be used as the generating-purpose water. Regardless of contained components, hardness, and liquid properties, any liquid including water may be used as the generating-purpose water in the present invention.

Hydrogen generating system storing container in the present invention is characterized by isolating the hydrogen generating system from the living organism applicable fluid and sending hydrogen gas, which has been generated in the hydrogen generating system storing container, to the living organic applicable fluid via an exhaust outlet of the hydrogen generating system storing container. The equipment of the present invention including the hydrogen generating system storing container can be accommodated in a closed container so as to be a separate apparatus from the closed container for accommodating it or to be a structural site having been preliminarily incorporated in the closed container.

The hydrogen bubble forming implement of the present invention is characterized by isolating the hydrogen generating system from the living organism applicable fluid and sending hydrogen gas, which has been generated in the hydrogen bubble Forming implement, to the living organic applicable fluid via a gas/liquid separating section of the hydrogen bubble forming implement. The equipment of the present invention including the hydrogen bubble forming implement can be accommodated in a closed container so as to be a separate apparatus from the closed container for accommodating it or to be a structural site having been preliminarily incorporated in the closed container.

Such a gas/liquid separating section is characterized, for example, by being devised such that a valve (such as a check valve or a ball valve), a gas permeable film or the like is included as a component or material thereby to vent hydrogen gas generated by the contact reaction between the hydrogen generating system and the generating-purpose water and to substantially avoid the generating-purpose water from flowing out and/or to avoid the living organism applicable fluid from flowing in.

Such devising involves, for example, providing a valve in the gas/liquid separating section to prevent the living organism applicable fluid from flowing into the hydrogen bubble forming implement. This allows for preventing water having flowed into the hydrogen bubble forming implement from flowing out again to the living organism applicable fluid at the time of shaking and the like, while the hydrogen gas generated in the hydrogen bubble forming implement is capable of being released into the living organism applicable fluid. More specifically, such a valve provided in the gas/liquid separating section is an open-close type valve which separates the internal and external of the hydrogen bubble forming implement, and which is to be opened by a gas pressure of the hydrogen gas generated in the internal of the hydrogen bubble forming implement owing to the reaction between the hydrogen generating system and the generating-purpose water thereby to exhaust the hydrogen gas into the external of the hydrogen bubble forming implement, while to be naturally or artificially closed after the exhaust through the gravity force or the water pressure from the external of the hydrogen bubble forming implement. The valve is characterized by substantially not causing the organism-applicable fluid existing at the external of the hydrogen bubble forming implement to flow into the internal thereof except for during the exhaust of the hydrogen gas.

Figure 1B:
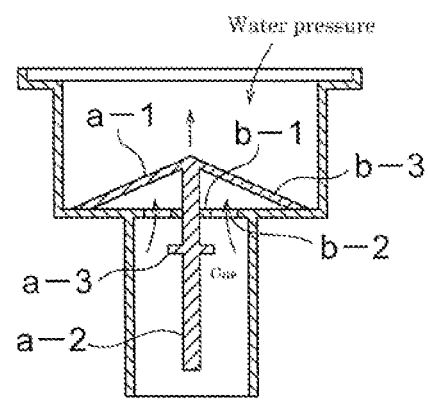
FIG. 1B is a cross-sectional view illustrating the gas/liquid separating section according to one embodiment of the present invention.

FIG. 1 illustrates an example of the gas/liquid separating section employing such an open-close type valve. In this case, the gas/liquid separating section is comprised of an open-close type valve (a) and a recessed component (b) made of plastic with which the valve is combined. The open-close type valve is configured such that one axial part (a-2) extends from a lampshade-like head part (a-1) while an annular flange (a-3) is shaped at a midway along the axial part so as to surround it. In addition, the recessed component is configured such that the base plate thereof is formed therein with a center hole (b-1) and three holes (b-2) each spread out in a fan-like form are opened to surround the center hole (b-1), while an edge (b-3) remains as a peripheral portion of the base plate to be engaged with the head part of the valve. This base plate has an area with such an extent that the head part (a-1) of the valve is just stored, and when the head part (a-1) of the valve has been stored, the axial part (a-2) of the valve is allowed to pass through the above-described center hole (b-1) opened at the center portion, whereas the annular flange (a-3) surrounding the axial part is not allowed to easily pass therethrough due to its size. However, if the axial part (a-2) having passed through the center hole (b-1) opened at the center portion of the base plate of the recessed component is pulled down from below, then the annular flange (a-3) surrounding the axial part of the valve passes through the hole (b-1) of the base plate while being deformed, thereby combining the valve (a) and the recessed component (b).

As the gas pressure of hydrogen gas generated in the hydrogen bubble forming implement increases, the hydrogen gas is exhausted while the head part of the open-close type valve having been located at the base plate of the recessed component is pressed and opened, but the annular flange surrounding the axial part is engaged with the center hole opened at the center portion of the base plate of the recessed component, and the open-close valve is thus prevented from dropping off from the recessed component even due to the hydrogen gas pressure during the exhaust.

In addition to this, by further decreasing the amount of the generating-purpose water to be introduced into the hydrogen bubble forming implement, the generating-purpose water is prevented from flowing out into the living organism applicable fluid even during the exhaust of hydrogen gas from the valve.

With respect to a target of the usage of the generating-purpose water, when the hydrogen generating system is removed (in the case where the hydrogen generating system is covered by a covering material as will be described later, removed with the covering material) after having introduced the generating-purpose water into the hydrogen bubble forming implement storing the hydrogen generating system, it is desirable that the amount of the generating-purpose water remaining in the hydrogen bubble forming implement is 10 cc or less, preferably 5 cc or less, more preferably 3 cc or less, and most preferably 1 cc or less. Moreover, for the sake of avoiding the flowing out of such excess generating-purpose water, it is desirable that substances or materials having water absorbability, such as absorbent beads, ion-exchange resin (dry ion-exchange resin is further preferable because of higher water absorbability as will be described later), absorbent paper, hyaluronic acid, and polyacrylic acid, are involved in the hydrogen bubble forming implement or in the covering material as will be described later, etc.

Note that, a part or whole of the hydrogen bubble forming implement may be configured of such a gas/liquid separating section. It is desirable that materials provided with the hydrogen bubble forming implement for parts other than the gas/liquid separating section are those, such as acrylic resin, which are scarcely permeated with water and hard to be corroded by water.

Another devising involves, for example, providing the gas/liquid separating section with a hydrogen permeable film which allows water to flow into the hydrogen bubble forming implement while preventing water to flow out from the hydrogen bubble forming implement, i.e. controls inflow and outflow of water irreversibly. By contacting the equipment for producing living organism applicable hydrogen-contained fluid having such a gas/liquid separating section with the living organism applicable fluid, a part of the living organism applicable fluid flows into the hydrogen bubble forming implement via the gas/liquid separating section. The living organism applicable fluid having flowed thereto reacts as the generating-purpose water with the hydrogen generating system in the hydrogen bubble forming implement thereby to generate hydrogen gas. This causes the generated hydrogen gas to be released into the living organism applicable fluid while avoiding the generating-purpose water to flow into the living organism applicable fluid owing to the block by the film.

In addition, the present invention may involve a covering material such as nonwoven fabric for further covering solid constituents such as the hydrogen generating agent included in the hydrogen generating system in order to ensure the separation between the living organism applicable fluid and the hydrogen generating system. Such a covering material is characterized by allowing hydrogen gas and water to permeate therethrough and not allowing the hydrogen generating system and its reaction residues to pass therethrough. It is desirable that the pore size of such a covering material is 1,000 µm or less, preferably 500 µm or less, more preferably 150 µm or less, and most preferably 50 µm or less.

Beside that, it is desirable that the average grain diameter of the hydrogen generating agent such as metal magnesium in the present invention is a diameter which is enough not to pass those grains through the covering material to the outside and enables to increase the activity thereof by microparticulation. For example, it is desirable that the average grain diameter of the hydrogen generating agent is 3,000 µm or less, preferably 1,000 µm or less, more preferably 500 µm or less, and most preferably 250 µm or less.

The hydrogen generating system in the present invention may contain agents, such as sequestering agent and pH adjuster, which accelerate the hydrogen generating reaction, in addition to the hydrogen generating agent.

Such a sequestering agent contains one or more substances for generating one or more substances which are absolutely undissolved or scarcely dissolved in water and has a property for adsorbing metal ions in the hydrogen bubble forming implement or the covering material. Insoluble or poorly-soluble metal sequestering agents such as cation exchange resin are preferably used. Among them, hydrogen ion type cation exchange resins are more preferred because of having an additional function as pH adjuster, wherein the hydrogen ion type cation exchange resins include an acidic cation exchange resin having sulfonic acid group as exchange group and an acidic cation exchange resin having carboxylic acid group as exchange group, both of which adsorb metal ions and release hydrogen ions ($H^+$).

Examples of the pH adjuster in the present invention include substances having properties for inhibiting (neutralizing or preventing the generation of hydroxide ions ($OH^-$) by supplying hydrogen ions ($H^+$), such as citric acid, adipic acid, malic acid, acetic acid, succinic acid, gluconic acid, lactic acid, phosphoric acid, hydrochloric acid, sulfuric acid, and other acids, and further include substances for removing hydroxide ions by being subjected to hydrolysis to form insoluble hydroxide. Mineral ores including aluminum ions, and other pH adjusters which form insoluble hydroxide by being subjected to hydrolysis are preferably used. Among them, alums such as aluminum ammonium sulfate are more preferred because they generate insoluble aluminum hydroxide by being subjected to hydrolysis while having an additional function as sequestering agent (flocculant or aggregating agent) for magnesium ions and calcium ions.

As described above, hydrogen ion type cation exchange resins and alums are preferred substances which have both functions as sequestering agent and as adjuster even by one agent.

In addition, it is preferred that, in order to suppress time degradation of the hydrogen generating agent, the hydration number and the water content ratio of the substances, such as sequestering agent and pH adjuster, contained in the hydrogen generating system are lower. More specifically, with respect to the hydration number, it is desirable to be trihydrate or lower, preferably dihydrate or lower, more preferably monohydrate or lower, and most preferably nonhydrate or anhydride. It is also desirable that the water content ratio is 40 weight % or less, preferably 30 weight % or less, more preferably 20 weight % or less, and most preferably 15 weight % or less.

The living organism applicable high concentration hydrogen-contained fluid in the present invention includes a living organism applicable hydrogen-contained fluid of which the dissolved hydrogen concentration in the fluid is 0.1 ppm or more, and preferably 1.0 ppm or more. The living organism applicable supersaturated hydrogen-contained fluid in the present invention involves a situation where the dissolved hydrogen concentration is higher than or equal to the degree of solubility at ordinary temperatures and pressures, and includes a living organism applicable high concentration hydrogen-contained fluid of 1.6 ppm or more, 2.0 ppm or more, 3.0 ppm or more, 4.0 ppm or more, 5.0 ppm or more, 6.0 ppm or more, 7.0 ppm or more, 8.0 ppm or more, 9.0 ppm or more, and 10.0 ppm or more.

Note that the selective hydrogen adding equipment for living organism applicable fluid according to the present invention, which is configured by accommodating the hydrogen generating system into the hydrogen bubble forming implement, may be disposed within the closed container for storing the living organism applicable fluid so as to be in the living organism applicable fluid, in the air space of the closed container, or in the outer space of the closed container.

The hydrogen gas generated in the hydrogen bubble forming implement by the reaction between the hydrogen generating system and the generating-purpose water is released via the gas/liquid separating section of the hydrogen bubble forming implement into the closed container storing the living organism applicable fluid and forms a hydrogen gas phase of high pressure and high concentration. Note that the applicant(s) have found out that, even when the selective hydrogen adding equipment for living organism applicable fluid according to the present invention is disposed in the living organism applicable fluid, most of the generated hydrogen molecules first transfer toward the air space of the closed container without dissolving into the living organism applicable fluid.

Further to say, the applicant(s) have found out that, when the hydrogen generating agent is disposed in the living organism applicable fluid after stored in the hydrogen bubble forming implement, the amount of hydrogen dissolving into the living organism applicable fluid after putting them into the fluid is further less than the case where the hydrogen generating agent is put in a hared state into the living organism applicable fluid without being stored in the hydrogen bubble forming implement.

That is, hydrogen molecules generated from the hydrogen generating agent not stored in the hydrogen bubble forming implement come to form clusters or microscopic bubbles while directly dissolving into the living organism applicable fluid, whereas, when hydrogen molecules are released into the living organism applicable fluid via the gas/liquid separating section of the hydrogen bubble forming implement, the hydrogen bubble forming implement acts as a kind of stopper for the hydrogen gas, thereby resulting in that the hydrogen molecules once gather together in an appropriate amount at the vicinity of the inner wall of the gas/liquid separating section and are thereafter released as hydrogen gas bubbles from the gas/liquid separating section. In other words, when released into the living organism applicable fluid, the hydrogen molecules are released as hydrogen gas bubbles already having certain dimensions.

This is visually observed. For example, if the selective hydrogen adding equipment for living organism applicable fluid according to the present invention is disposed in the closed container storing the living organism applicable fluid and the container is left for a while in a laid form, then the hydrogen gas generated in the hydrogen bubble forming implement releases intermittently hydrogen bubbles from the gas/liquid separating section while causing the volume of the hydrogen gas phase to be progressively increased. In other words, the released hydrogen gas is of large bubble size, therefore moving upward in water to rapidly transfer into the gas phase in the closed container.

In general, among ones of ordinary skill in the art of producing not only hydrogen-contained solution but other gas-contained solution with expectation of some form of industrial use, it has been considered that the important thing for producing a high-concentration gas solution is to make the bubble size of the gas be microscopic as much as possible thereby decreasing the rising velocity of the bubbles toward the gas phase. At the time of the present application, it still remains to be recognized as one of primary technical issues in the art to make various industrial gasses including hydrogen, oxygen or ozone be micro-bubbles and possibly nano-bubbles.

Meanwhile, the inventors have found out that, in the case that consumers attempt to obtain a living organism applicable high concentration hydrogen-contained fluid at various locations, such as home, workplace, street, and storefront, it is far more desirable to form first, the hydrogen gas phase in the closed container and increase the internal pressure in the container thereafter appropriately shaking the closed container to collect the hydrogen gas from the gas phase, than directly dissolving hydrogen molecules into the living organism applicable fluid in the closed container which stores the living organism applicable fluid including drinking water and beverages, such as tea and coffee.

According to experiments by the inventors, in spite of the fact that the dissolved hydrogen concentration in the living organism applicable fluid increases up to approximately 0.7 ppm after a lapse of 10 minutes from a situation where metal magnesium as the hydrogen generating agent has been disposed in the living organism applicable fluid in the closed container without being stored in the hydrogen bubble forming implement, subsequent shaking of the closed container only increases the dissolved hydrogen concentration up to approximately 0.9 ppm (approximately 1.3 times). In contrast, the dissolved hydrogen concentration in the living organism applicable fluid slightly increases up to approximately 0.2 ppm after a lapse of 10 minutes from a situation where the same amount of metal magnesium as the hydrogen generating agent has been disposed in the living organism applicable fluid in the closed container with being stored in the hydrogen bubble forming implement, whereas subsequent shaking of the closed container drastically increases the dissolved hydrogen concentration up to approximately 3.0 ppm (approximately 15 times).

Thus, it is desirable to accommodate in the closed container the hydrogen adding equipment for living organism applicable fluid according to the present invention, which is configured by storing the hydrogen generating system and the generating-purpose water in the hydrogen bubble forming implement, and to appropriately shake the closed container, for the purpose of increasing the dissolved hydrogen concentration in the living organism applicable hydrogen-contained fluid.

In this case, the closed container in the present invention is intended to include a container which is devised not to expose the contents in the container to the air. Examples of the closed container include containers with lids, such as PET bottles and aluminum bottles with caps. It is desirable that the container has a portable form and volume in order for a person to easily shake it in his/her hand. It is also desirable that the container is of 2 L or less, preferably 1 L or less, and most preferably 0.5 L or less, but not limited thereto.

Preferred materials for the container are to have low hydrogen permeability. As the hydrogen permeability is lower, the generated hydrogen is hard to escape from the container system.

The hydrogen permeability of the closed container in the present invention is measured as follows. That is, with reference to the method described in Patent Application No. 2009-221.567 or the like, hydrogen dissolved water is prepared to stably keep approximately the saturated concentration (1.6 ppm at 20 degrees C. and 1 atm) with the volume of 20 times of the inner volume of a closed container as an object to be measured, and the closed container is then immersed during 5 hours in the hydrogen dissolved water after being fully filled with clarified water (charcoal-treated water, such as tap water available from Fujisawa city water-service treated to pass through a charcoal column).

Thereafter, the dissolved hydrogen concentration in the clarified water is measured, wherein the container of lower hydrogen permeability in the present invention involves a closed container with dissolved hydrogen concentration of 1,000 ppb or lower, preferably 500 ppb or lower, more preferably 100 ppb or lower, and most preferably 1.0 ppb or lower.

It is desirable that the closed container has a pressure-proof property capable of resisting the increasing of the inner pressure due to the generation of hydrogen. Specifically, it is desirable to be a pressure-proof container capable of resisting the inner pressure of 0.11 MPa as absolute pressure, preferably 0.4 MPa, more preferably 0.5 MPa, and most preferably 0.8 MPa. A PET bottle for carbonated drink may be preferably used. It is also desirable that the closed container comprises at the mouth thereof a mechanism for releasing the pressure (vent slot) midway through opening the cap for the purpose of safety opening.

The shaking in the present invention is to give a physical impact or shock to the closed container thereby replacing the dissolved gas such as dissolved oxygen in the living organism applicable fluid with hydrogen gas while contacting the living organism applicable fluid and the gas-phase hydrogen with each other in the closed container. The shaking in the present invention involves natural shaking using hand or hands as well as artificial shaking using a machine. Examples of such artificial shaking include shaking by using a shaking machine, an agitator, an ultrasonic generator, and other apparatuses.

Moreover, in order for hydrogen gas to be further accumulated in the gas phase in the closed container, it is desirable to start the shaking after 1 minute has elapsed, preferably 2 minutes, more preferably 4 minutes, furthermore preferably 8 minutes, and most preferably 1.0 minutes, from the time when the selective hydrogen adding equipment for living organism applicable fluid according to the present invention was disposed in the closed container.

Note that an exemplary case of the natural shaking in the present invention is as follows. That is, the shaking is performed by a Japanese man of 30's having an average physical size, who holds the middle portion of the closed container by his dominant hand and moves only the wrist to shake it such that the cap forms into an arch above the wrist with a pace of 2 strokes per second, total 120 strokes.

Further, in order to accelerate the dissolution of the high-pressure and high-concentration hydrogen gas into the living organism applicable fluid, it is desirable that the time period of the shaking is 5 seconds or longer for the natural shaking, preferably 10 seconds or longer, more preferably 15 seconds or longer, and still preferably 30 seconds or longer.

In addition, considering the facility in shaking, the closed container is provided therein with a head space of 15% or less with respect to the container volume, preferably 10% or less, and most preferably 5% or less even after being filled with the living organism applicable fluid.

Moreover, it is preferred that the shaking is such that, when performing the shaking after disposing the selective hydrogen adding equipment for living organism applicable fluid according to the present invention in the living organism applicable fluid, the dissolved hydrogen concentration in the living organism applicable fluid is enhanced twice or higher of the dissolved hydrogen concentration before the shaking, preferably 3 times or higher, more preferably 4 times or higher, 5 times or higher, 6 times or higher, 7 times or higher, 8 times or higher and 9 times or higher in this order, and further preferably 10 times or higher.

Furthermore, it is preferred that the inner pressure in the closed container before the shaking is equal to or higher than the atmosphere pressure in order to obtain higher concentration living organism applicable hydrogen-contained fluid, such as supersaturated living organism applicable hydrogen-contained fluid with 1.6 ppm or higher. The solubility of hydrogen molecules to the living organism applicable fluid increases as the inner pressure loaded by the generated hydrogen molecules to the closed container increases, and exceeds the solubility at the normal temperature and pressure in due time. The reason why the closed container storing the hydrogen generating system is left for a while for example in the examples as will be described later is to pressurize the closed container from the inside by the generated hydrogen gas, and also to allow for appropriately shaking the closed container under the increased pressure thereby further accelerating the dissolution of the hydrogen molecules to the living organism applicable hydrogen-contained fluid.

Meanwhile, by being combined with hydrogen generating agents containing metals having higher ionization tendency than hydrogen, such as metal magnesium, or hydrogenated metals, insoluble high molecular substances having sequestering functionality and pH adjusting functionality, such as the above-described hydrogen ion type cation exchanger resin, may constitute an effective hydrogen generating system in which three functionalities of hydrogen generating, sequestering and pH adjusting are closely associated with one another. As an example, the hydrogen generating system configured of metal magnesium and hydrogen ion type cation exchanger resin will hereinafter be described.

In general, if metal magnesium is contacted with the living organism applicable fluid, hydrogen molecule and magnesium hydroxide are generated in accordance with the following formula (1).

$$Mg+2H_2O \rightarrow Mg(OH)_2+H_2 \quad \text{Formula (1)}$$

As the reaction mechanism thereof, elementary reactions are considered:

$$Mg \rightarrow Mg^{2+}+2e^- \quad \text{Formula (2)}$$

wherein electrons are released from metal magnesium;

$$2H_2O+2e^- \rightarrow 2OH^-+H_2 \quad \text{Formula (3)}$$

wherein the electrons derived from the metal magnesium reduce water molecules to generate hydrogen molecule and hydroxide ions; and

$$2H^++2e^- \rightarrow H_2 \quad \text{Formula (4)}$$

wherein the electrons derived from the metal magnesium reduce hydrogen ions to generate hydrogen molecule.

Here, if hydrogen ion type cation exchanger resin is present in the vicinity of metal magnesium, then the magnesium ion released in accordance with Formula (2) is adsorbed to the hydrogen ion type cation exchanger resin and hydrogen ions are released from the hydrogen ion type cation exchanger resin. Therefore, electrons released in accordance with Formula (2) preferentially reduce such adjacent hydrogen ions rather than reduce water molecules.

Thus, in the hydrogen generating system of the present invention, hydrogen is preferentially generated in accordance with Formula (4) which is a hydrogen generating reaction not to generate hydroxide ions rather than in accordance with Formula (3) which is a hydrogen generating reaction to generate hydroxide ions. Consequently, the hydrogen generating reaction may be readily accelerated because magnesium ions and hydroxide ions are liable to be maintained as being constantly decreased in the system.

Note that the condition of not changing the constituents of the living organism applicable fluid in the present invention includes concepts, such as, but not limited to, not changing the total hardness and/or pH of the living organism applicable fluid.

Here, the condition of not changing the total hardness of the living organism applicable fluid includes the following cases, but is not limited thereto.

That is, such cases include a case where a PET bottle for carbonated drink (about 530 cc volume when filled with full water to the mouth) is substantially filled with 515 cc of living organism applicable fluid as being clarified water obtained by dechlorination treating of tap water and having total hardness (Ca hardness+Mg hardness) of approximately 55 to 65 ppm (clarified water such as obtained by treating tap water available from Fujisawa city water-service to pass through a charcoal column), the nondestructive producing equipment for high-concentration hydrogen solution according to the present invention is disposed in the living organism applicable fluid, the bottle is left to be laid flat during 10 minutes, and the total hardness of the solution after performing typical and natural shaking (holding the middle portion of the PET bottle by one's dominant hand and moving only the wrist such that the cap forms into an arch above the wrist with a pace of 2 strokes per second, total 120 strokes) is from (the total hardness of the original water minus 25 ppm) to (the total hardness of the original water plus 25 ppm), preferably from (the total hardness of the original water minus 15 ppm) to (the total hardness of the original water plus 15 ppm), and most preferably from (the total hardness of the original water minus 10 ppm) to (the total hardness of the original water plus 10 ppm).

Here, the condition of not changing the pH of the living organism applicable fluid includes the following cases, but is not limited thereto.

That is, such cases include a case where a PET bottle for carbonated drink (about 530 cc volume when filled with full water to the mouth) is substantially filled with about 515 cc of living organism applicable fluid as being clarified water obtained by dechlorination treating of tap water and having pH of approximately 7.0 to 7.8 (clarified water such as obtained by treating tap water available from Fujisawa city water-service to pass through a charcoal column), the nondestructive producing equipment for high-concentration hydrogen solution according to the present invention is disposed in the living organism applicable fluid, the bottle is left to be laid flat during 10 minutes, and the pH of the solution after performing typical and natural shaking (holding the middle portion of the PET bottle by one's dominant hand and moving only the wrist such that the cap forms into an arch above the wrist with a pace of 2 strokes per second, total 120 strokes) is from (the pH of the original water minus 1.5) to (the pH of the original water plus 1.5), preferably from (the pH of the original water minus 1.0) to (the pH of the original water plus 1.0), and most preferably from (the pH of the original water minus 0.5) to (the pH of the original water plus 0.5).

EXAMPLES

Hereinafter, examples of the present invention will be described. Note that, when there is no particular explanation in the present application, various gauges used for measuring various physicality values are as follows: pH meter (including temperature indicator) manufactured by Horiba, Ltd. (main body type: D-13, probe type: 9620-10D); and DH meter (dissolved hydrogen meter) manufactured by DKK-Toa Corporation (main body type: DHDI-1, electrode (probe) type: HE-5321, transponder type: DHM-F2).

Calcium hardness and magnesium hardness were measured by Calmagite colorimetric method using water quality analyzer DR/4000 (manufactured by HACH Company).

Example 1

Figure 2:
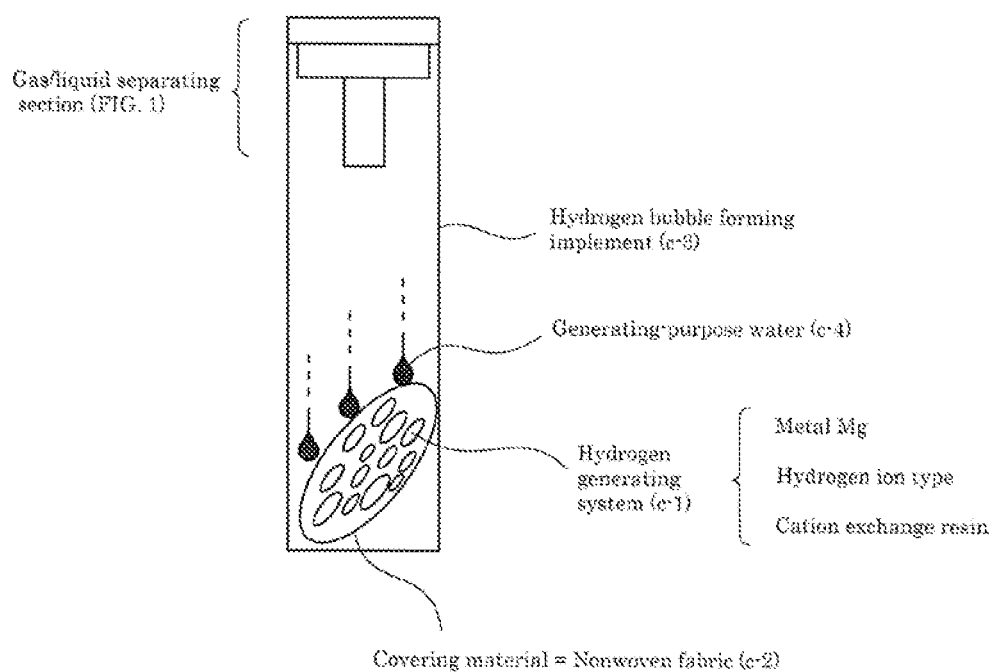
FIG. 2 is a front elevational view illustrating a selective hydrogen adding equipment in which the gas/liquid separating section shown in FIG. 1 is attached to a hydrogen bubble forming implement.

Illustrated as FIG. 2

A hydrogen generating system (c-1) containing 300 mg of metal magnesium (MG100: Kanto Metal Corporation) as the hydrogen generating agent and further containing 1,500 mg of hydrogen ion type cation exchange resin (obtained by thermally-drying "DIAION Ion Exchange Resin SK1BH: Mitsubishi Chemical Corporation", a commercially available strongly acidic ion exchange resin H-type product) was enclosed and heat sealed in a nonwoven fabric (Precise Regular C5160: Asahi Kasei Corporation) (c-2), and then stored in an acrylic resin tubular hydrogen bubble forming implement (c-3) with that nonwoven fabric. The selective hydrogen adding equipment for living organism applicable fluid according to the present invention was obtained by dropping generating-purpose water (c-4) into the hydrogen bubble forming implement with such an extent of wetting the nonwoven fabric, and closing the opening of, the hydrogen bubble forming implement with the gas/liquid separating section (FIG. 1).

Subsequently, a PET bottle for carbonated drink (about 530 cc volume when filled with full water to the mouth) was substantially filled with about 515 cc of clarified water (charcoal-treated water obtained by treating tap water available from Fujisawa city waterservice to pass through a charcoal column), and the selective hydrogen adding equipment for living organism applicable fluid was then disposed into the clarified water in the PET bottle.

Thereafter, the bottle was left to be laid flat during 10 minutes, and one of the present inventors (Japanese man of 30's having an average physical size) then held the middle portion of the PET bottle by his dominant hand and moved only the wrist to shake it such that the cap was forming into an arch above the wrist with a pace of 2 strokes per second, total 120 strokes (total 60 seconds).

Measurements were done for pH, dissolved hydrogen concentration, calcium (Ca) hardness, and magnesium (Mg) hardness of contained fluid before and after shaking.

Example 2

Figure 3:
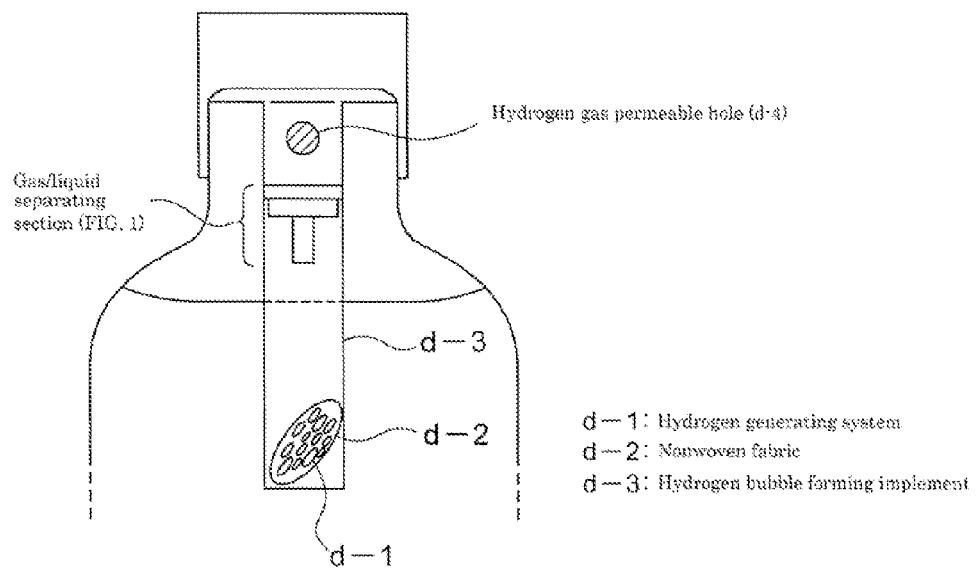
FIG. 3 is a front elevational view illustrating another example of selective hydrogen adding equipment in which the gas/liquid separating section shown in FIG. 1 is attached to a hydrogen bubble forming implement.

Illustrated as FIG. 3

A hydrogen generating system (d-1) containing 300 mg of metal magnesium (MG100: Kanto Metal Corporation) as the hydrogen generating agent and further containing 1,500 mg of hydrogen ion type cation exchange resin (obtained by thermally-drying "DIAION Ion Exchange Resin SK1BH: Mitsubishi Chemical Corporation", a commercially available strongly acidic ion exchange resin H-type product) was enclosed and heat sealed in a nonwoven fabric (Precise Regular C5160: Asahi Kasei Corporation) (d-2), and then stored in an acrylic resin tubular hydrogen bubble forming implement (d-3) with that nonwoven fabric. The selective hydrogen adding equipment for living organism applicable fluid according to the present invention was obtained by dropping water into the hydrogen bubble forming implement with such an extent of wetting the nonwoven fabric, inserting the gas/liquid separating section described with reference to FIG. 1 to be disposed into the tubular hydrogen bubble forming implement so as just not to leave a space at the middle portion, and opening one or more hydrogen gas permeable holes (d-4) at a part of the outer wall of the hydrogen bubble forming implement.

Subsequently, a PET bottle for carbonated drink (about 530 cc volume when filled with full water to the mouth) was substantially filled with about 515 cc of clarified water (charcoal-treated water obtained by treating tap water available from Fujisawa city water-service to pass through a charcoal column), and the fringe of the hydrogen bubble forming implement was then caused to engage with the PET bottle mouth portion while the equipment was inserted into the mouth portion, and the cap was closed so as not to immerse the equipment in the water. At that time, the hydrogen gas permeable holes were positioned above the water level of the clarified water.

Thereafter, the bottle was left during 10 minutes, and one of the present inventors (Japanese man of 30's having an average physical size) then held the middle portion of the PET bottle by his dominant hand and moved only the wrist to shake it such that the cap was forming into an arch above the wrist with a pace of 2 strokes per second, total 120 strokes (total 60 seconds).

Measurements were done for pH, dissolved hydrogen concentration, calcium (Ca) hardness, and magnesium (Mg) hardness of contained fluid before and after shaking.

Example 3

A hydrogen generating system containing 300 mg of metal magnesium (MG100: Kanto Metal Corporation) as the hydrogen generating agent and further containing 900 mg of malic acid (DL-malic acid: FUSO CHEMICAL CO., LTD.) was enclosed with water absorbent paper and heat sealed in a nonwoven fabric (Precise Regular C5160: Asahi Kasei Corporation), and then stored in an acrylic resin tubular hydrogen bubble forming implement with that nonwoven fabric. The selective hydrogen adding equipment for living organism applicable fluid according to the present invention was obtained by dropping water into the hydrogen bubble forming implement with such an extent of wetting the nonwoven fabric, inserting a stopper made of water absorbent paper and in turn the gas/liquid separating section described with reference to FIG. 1 to be disposed into the tubular hydrogen bubble forming implement so as just not to leave a space at the middle portion, and opening one or more hydrogen gas permeable holes at a part of the outer wall of the hydrogen bubble forming implement.

Subsequently, a PET bottle for carbonated drink (about 530 cc volume when filled with full water to the mouth) was substantially filled with about 515 cc of clarified water (charcoal-treated water obtained by treating tap water available from Fujisawa city waterservice to pass through a charcoal column), and the fringe of the hydrogen bubble forming implement was then caused to engage with the PET bottle mouth portion while the equipment was inserted into the mouth portion, and the cap was closed so as not to immerse the equipment in the water. At that time, the hydrogen gas permeable holes were positioned above the water level of the clarified water.

Thereafter, the bottle was left during 10 minutes, and one of the present inventors (Japanese man of 30's having an average physical size) then held the middle portion of the PET bottle by his dominant hand and moved only the wrist to shake it such that the cap was forming into an arch above the wrist with a pace of 2 strokes per second, total 120 strokes (total 60 seconds).

Measurements were done for pH, dissolved hydrogen concentration, calcium (Ca) hardness, and magnesium (Mg) hardness of contained fluid before and after shaking.

Comparative Example 1

A hydrogen generating system was prepared to contain 300 mg of metal magnesium as the hydrogen generating agent and further contain 1,500 mg of hydrogen ion type cation exchange resin (obtained by thermally-drying "DIAION Ion Exchange Resin SK1BH: Mitsubishi Chemical Corporation", a commercially available strongly acidic ion exchange resin H-type product).

A PET bottle for carbonated drink (about 530 cc volume when filled with full water to the mouth) was substantially filled with about 515 cc of clarified water (charcoal-treated water obtained by treating tap water available from Fujisawa city water-service to pass through a charcoal column), and the hydrogen generating system was then put directly into the clarified water in the PET bottle.

Thereafter, the bottle was left during 10 minutes, and one of the present inventors (Japanese man of 30's having an average physical size) then held the middle portion of the PET bottle by his dominant hand and moved only the wrist to shake it such that the cap was forming into an arch above the wrist with a pace of 2 strokes per second, total 120 strokes (total 60 seconds).

Measurements were done for pH, dissolved hydrogen concentration, calcium (Ca) hardness, and magnesium (Mg) hardness of contained fluid before and after shaking.

Reference Example 1

Measurements were done for pH, dissolved hydrogen concentration, calcium (Ca) hardness, and magnesium (Mg) hardness of the clarified water used in the Examples and the Comparative Example.

Results are shown in Table 1.

TABLE 1

[Description of Reference Numerals]
a . . . valve
   a-1 . . . lampshade-like head part
   a-2 . . . axial part
   a-3 . . . flange
b . . . recessed component
   b-1 . . . center hole
   b-2 . . . fan-like hole
   b-3 . . . edge

What is claimed is:
1. An equipment for adding hydrogen into fluid applicable to a living organism comprising:
   a hydrogen generating system that contains a hydrogen generating agent, the hydrogen generating agent being hydrogenated metal or metal having higher ionization tendency than hydrogen;

a hydrogen bubble forming implement that stores the hydrogen generating system, the hydrogen bubble forming implement having a gas/liquid separating section including an open-close type valve; and
a closed container in which the fluid applicable to a living organism and the hydrogen bubble forming implement are stored,
wherein a fluid contained hydrogen is obtained by adding hydrogen gas into the fluid applicable to a living organism stored in the closed container through the open-close type valve the hydrogen gas is generated by a reaction between the hydrogen generating system and a generating-purpose water, and
the open-close type valve is opened by a gas pressure of hydrogen gas generated in an interior of the hydrogen bubble forming implement owing to the reaction thereby to exhaust hydrogen gas into the closed container on an exterior of the hydrogen bubble forming implement while the open-close type valve is closed after the hydrogen gas exhaust.

* * * * *